United States Patent [19]

Nakaguti et al.

[11] Patent Number: 4,694,004
[45] Date of Patent: Sep. 15, 1987

[54] SEMICARBAZIDE DERIVATIVES, PROCESSES FOR PREPARATION THEREOF AND PHARMACEUTICAL COMPOSITION COMPRISING THE SAME

[75] Inventors: Osamu Nakaguti; Norihiko Shimazaki, both of Toyonaka; Yoshio Kawai, Tokyo; Masashi Hashimoto, Takarazuka; Michie Nakatuka, Yokohama, all of Japan

[73] Assignee: Fujisawa Pharmaceutical Co., Ltd., Osaka, Japan

[21] Appl. No.: 746,510

[22] Filed: Jun. 19, 1985

[30] Foreign Application Priority Data

Jul. 9, 1984 [GB] United Kingdom ............... 8417453
May 7, 1985 [GB] United Kingdom ............... 8511553

[51] Int. Cl.⁴ .................. A61K 31/44; C07D 401/12; C07D 413/12; C07D 211/68
[52] U.S. Cl. .................. 514/228; 514/235; 514/272; 514/255; 514/252; 514/352; 514/336; 514/343; 514/342; 514/341; 514/338; 514/335; 514/332; 544/331; 544/131; 544/360; 546/283; 546/270; 546/280; 546/281; 546/331; 546/261; 546/279; 546/309; 546/265
[58] Field of Search .................. 544/331, 131, 360; 546/283, 270, 280, 281, 331, 261, 279, 309, 265, 308; 514/332, 335, 338, 341, 342, 343, 336, 352, 252, 255, 272, 228, 235

[56] References Cited

U.S. PATENT DOCUMENTS 4,088,653  5/1978  Knaus et al. ............... 260/295 AM

OTHER PUBLICATIONS

Wilcox, Journal of the Medicinal Chemistry, vol. 11, 171–172 (1968).
Yeung et al., Journal of the Medicinal Chemistry, vol. 25, 720–723 (1982).
Joshi et al., Chemical Abstracts, vol. 67, 108582p (1967).
Chemical Abstracts, vol. 71, 3166k (1969).
Bau–Hoi et al., Journal of the Chemical Society, (1956), 2160–2165.

Primary Examiner—John M. Ford
Attorney, Agent, or Firm—Oblon, Fisher, Spivak, McClelland & Maier

[57] ABSTRACT

A compound of the formula:

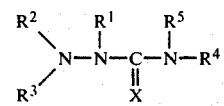

wherein
$R^1$ is hydrogen,
$R^2$ is hydrogen, lower alkyl, ar(lower)alkyl, lower alkenyl or aryl,
$R^3$ is lower alkyl, ar(lower)alkyl, lower alkenyl or aryl, or
$R^2$ and $R^3$ are taken together to form $(C_2-C_6)$-alkylidene group optionally substituted with aryl or taken together with the attached nitrogen atom to form a saturated or unsaturated, 5- or 6-membered heterocyclic group optionally substituted with aryl or lower alkyl; or
$R^1$ and $R^2$ are taken together with the attached nitrogen atoms to form a saturated or unsaturated, 5- or 6-membered heterocyclic group or 1,2-diazaspiroalkane-1,2-diyl group,
$R^3$ is hydrogen, lower alkyl, ar(lower)alkyl, lower alkenyl or aryl;
$R^4$ is lower alkyl optionally substituted with di(lower)alkylamino or a heterocyclic group, or a heterocyclic group optionally having suitable substituent(s),
$R^5$ is hydrogen or lower alkyl, and
X is O or S, and a pharmaceutically acceptable salt thereof may be used as anti-inflammatory and analgesic agents.

13 Claims, No Drawings

SEMICARBAZIDE DERIVATIVES, PROCESSES FOR PREPARATION THEREOF AND PHARMACEUTICAL COMPOSITION COMPRISING THE SAME

The present invention relates to novel semicarbazide derivatives and a pharmaceutically acceptable salt thereof. More particularly, it relates to novel semicarbazide derivatives and a pharmaceutically acceptable salt thereof which have antiinflammatory and analgesic activities, to processes for preparation thereof, to pharmaceutical composition comprising the same, and to a method of using the same therapeutically in the treatment of inflammation and various pains in human being and animals.

Accordingly, one object of this invention is to provide novel semicarbazide derivatives and a pharmaceutically acceptable salt thereof which are useful as antiinflammatory and analgesic agents.

Another object of this invention is to provide processes for preparation of said semicarbazide derivatives and a salt thereof.

A further object of this invention is to provide pharmaceutical composition comprising, as an active ingredient, said semicarbazide derivatives and a pharmaceutically acceptable salt thereof.

Still further object of this invention is to provide a method of using said semicarbazide derivatives and a pharmaceutically acceptable salt thereof in the treatment of inflammation and various pains in human being and animals.

Some N-substituted-1,2,3,6-tetrahydropyridine derivatives having antiinflammatory and analgesic activities have been known as described, for example, in U.S. Pat. No. 4,088,653 and Journal of Medicinal Chemistry Vol. 25, 720-723, 1982.

And some semicarbazide derivatives having similar chemical structure to the object compounds of this invention have been known as described, for example, in Journal of Medicinal Chemistry Vol. 11, 171-172, 1968, Journal of Chemical Society 1956, 2160-2165 and France Patent No. 1,521,959. But it has not been known that these compounds possess antiinflammatory and analgesic activities.

The semicarbazide derivatives of the present invention are novel and can be represented by the following general formula [I]:

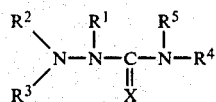

[I]

wherein
$R^1$ is hydrogen,
$R^2$ is hydrogen, lower alkyl, ar(lower)alkyl, lower alkenyl or aryl,
$R^3$ is lower alkyl, ar(lower)alkyl, lower alkenyl or aryl, or
$R^2$ and $R^3$ are taken together to form ($C_2$-$C_6$)-alkylidene group optionally substituted with aryl or taken together with the attached nitrogen atom to form a saturated or unsaturated, 5- or 6-membered heterocyclic group optionally substituted with aryl or lower alkyl; or
$R^1$ and $R^2$ are taken together with the attached nitrogen atoms to form a saturated or unsaturated, 5- or 6-membered heterocyclic group or 1,2-diazaspiroalkane-1,2-diyl group,
$R^3$ is hydrogen, lower alkyl, ar(lower)alkyl, lower alkenyl or aryl;
$R^4$ is lower alkyl optionally substituted with di(lower)alkylamino or a heterocyclic group, or a heterocyclic group optionally having suitable substituent(s),
$R^5$ is hydrogen or lower alkyl, and
X is O or S.

The object compound [I] and its pharmaceutically acceptable salt can be prepared by the following processes.

Process 1

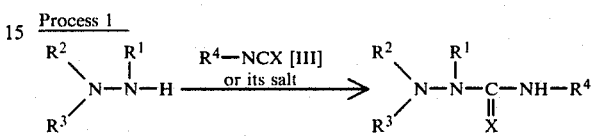

[II]
or its salt

[Ia]
or its salt

Process 2

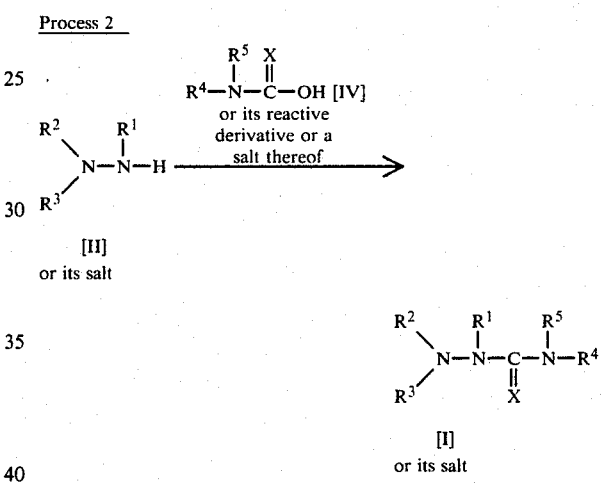

[II]
or its salt

[I]
or its salt

Process 3

[V]
or its reactive derivative or a salt thereof

[I]
or its salt

Process 4

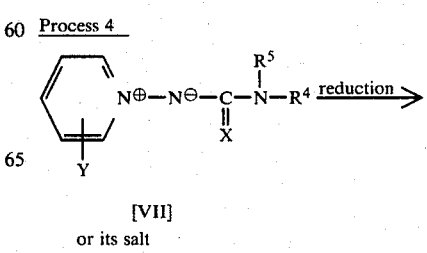

[VII]
or its salt

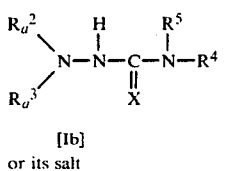

[Ib]
or its salt

Process 5

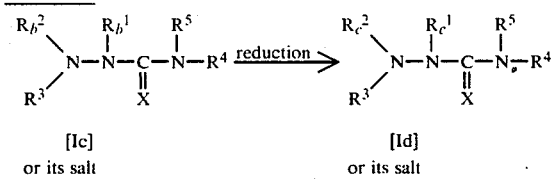

[Ic]          [Id]
or its salt   or its salt wherein
$R^1$, $R^2$, $R^3$, $R^4$, $R^5$ and X are each as defined above,
Y is hydrogen, aryl or lower alkyl,
$R_a^2$ and $R_a^3$ are taken together with the attached nitrogen atom to form a partially or fully saturated pyridin-1-yl group optionally substituted with aryl or lower alkyl,
$R_b^1$ and $R_b^2$ are taken together with the attached nitrogen atoms to form unsaturated 5- or 6-membered heterocyclic group, and
$R_c^1$ and $R_c^2$ are taken together with the attached nitrogen atoms to form a partially or fully saturated 5- or 6-membered heterocyclic group.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" may be a straight or branched one such as methyl, ethyl, propyl, isopropyl, butyl, isobutyl, t-butyl, pentyl, hexyl, or the like, in which the preferred one may be $C_1$–$C_4$ alkyl.

Suitable "lower alkenyl" may be vinyl, allyl, 1-propenyl, 3-butenyl, 4-pentenyl, 5-hexenyl, or the like, in which the preferred one may be $C_2$–$C_4$ alkenyl.

Suitable "lower alkoxy" may be methoxy, ethoxy, propoxy, isopropoxy, butoxy, isobutoxy, t-butoxy, pentyloxy, hexyloxy, or the like, in which the preferred one may be $C_1$–$C_4$ alkoxy.

Suitable "aryl" may be phenyl, naphthyl or the like.

Suitable "ar(lower)alkyl" may be benzyl, phenethyl, phenylpropyl, benzhydryl, trityl, or the like, in which the preferred one may be phenyl($C_1$–$C_4$)alkyl.

Suitable "($C_2$–$C_6$)alkylidene group" may be ethylidene, propylidene, isopropylidene, butylidene, pentylidene, hexylidene or the like. These ($C_2$–$C_6$)alkylidene groups may be substituted with aryl group(s), wherein said aryl group(s) may have suitable substituent(s). Suitable examples of the aryl group optionally having substituent(s) may be phenyl, 2-tolyl, 4-chlorophenyl, naphthyl, or the like.

Accordingly, suitable examples of the ($C_2$–$C_6$)-alkylidene group having such substituent(s) may be 1-phenylethylidene, 2-phenylethylidene, 1,2-diphenylethylidene, 1-phenylpropylidene, 1-(4-chlorophenyl)ethylidene, or the like.

Suitable "saturated or unsaturated, 5- or 6-membered heterocyclic group" formed by $R^2$, $R^3$ and the attached nitrogen atom may be pyrrolidin-1-yl, morpholino, piperidino, piperazin-1-yl, pyrrolin-1-yl, 1,4-dihydropyridin-1-yl, 1,2-dihydropyridin-1-yl, 1,2,3,6-tetrahydropyridin-1-yl or the like. These heterocyclic groups may be substituted with aryl or lower alkyl, suitable examples of which are as exemplified before.

Suitable "partially or fully saturated pyridin-1-yl group" may be piperidino, 1,4-dihydropyridin-1-yl, 1,2-dihydropyridin-1-yl or 1,2,3,6-tetrahydropyridin-1-yl. Said heterocyclic groups may be substituted with aryl or lower alkyl, suitable examples of which are as exemplified before.

Suitable "saturated or unsaturated, 5- or 6-membered heterocyclic group" formed by $R^1$, $R^2$ and the attached nitrogen atoms may be pyrazolidinyl, perhydropyridazinyl, pyrazolinyl, 1,2,3,4-tetrahydropyridazinyl, 1,2,3,6-tetrahydropyridazinyl, or the like.

Suitable "unsaturated 5- or 6-membered heterocyclic group" may be 1,2,3,6-tetrahydropyridazinyl, 1,2,3,4-tetrahydropyridazinyl, 1,2-dihydropyridazinyl, or the like.

Suitable "partially or fully saturated 5- or 6-membered heterocyclic group" may be 1,2,3,6-tetrahydropyridazinyl, perhydropyridazinyl, or the like.

Suitable "1,2-diazaspiroalkane-1,2-diyl group" may be 1,2-diazaspiro[2.5]octane-1,2-diyl, 1,2-diazaspiro[2.6]nonane-1,2-diyl, 1,2-diazaspiro[4.5]decane-1,2-diyl, or the like.

Suitable "heterocyclic group" may be saturated or unsaturated, monocyclic or polycyclic heterocyclic group containing at least one hetero-atom selected from oxygen, sulfur and nitrogen atoms. Preferable heterocyclic group may be unsaturated, 3 to 8-membered, more preferably 5 or 6-membered heteromonocyclic group containing 1 to 4-nitrogen atom(s), for example, pyrrolyl [e.g. 2-pyrrolyl, etc.], pyrrolinyl [e.g. 2-pyrrolin-3-yl, etc.], imidazolyl [e.g. 2-imidazolyl, 4-imidazolyl, etc.], imidazolinyl [e.g. 2-imidazolin-4-yl, etc.] pyrazolyl [e.g. 3-pyrazolyl, 4-pyrazolyl, etc.], pyridyl [e.g. 2-pyridyl, 3-pyridyl and 4-pyridyl], pyridyl N-oxide, pyridinio, dihydropyridyl, tetrahydropyridyl [e.g. 1,2,3,6-tetrahydropyridyl, etc.], pyrimidinyl [e.g. 2-pyrimidinyl, 4-pyrimidinyl, etc.], pyrazinyl, pyridazinyl [e.g. 3-pyridazinyl, 4-pyridazinyl, etc.], triazolyl [e.g. 1H-1,2,4-triazol-3-yl, 1H-1,2,3-triazol-4-yl, 2H-1,2,3-triazol-4-yl, etc.], tetrazolyl [e.g. 1H-tetrazol-5-yl, 2H-tetrazol-5-yl, etc.] etc.;

saturated, 3- to 8-membered, more preferably 5 or 6-membered heteromonocyclic group containing 1 to 4 nitrogen atom(s), for example, pyrrolidinyl [e.g. 1-pyrrolidinyl, 2-pyrrolidinyl, etc.], imidazolidinyl [e.g. imidazolidin-2-yl, etc.], piperidyl [e.g. 2-piperidyl, etc.], piperidino, piperazinyl [e.g. 1-piperazinyl, 2-piperazinyl, etc.], pyrazolidinyl [e.g. 2-pyrazolidinyl, etc.], etc.;

unsaturated, condensed heterocyclic group containing 1 to 5 nitrogen atom(s), for example, indolyl, isoindolyl, indolizinyl, benzimidazolyl, quinolyl, isoquinolyl, indazolyl, benzotriazolyl, 6,7-dihydro-5H-1-(1-pyrindinio), etc.;

unsaturated, 3 to 8-membered heteromonociclic group containing 1 to 2 oxygen atom(s) and 1 to 3 nitrogen atom(s), for example, oxazolyl, isoxazolyl, oxadiazolyl [e.g. 1,2,4-oxadiazolyl, 1,3,4-oxadiazolyl, 1,2,5-oxadiazolyl], etc.;

saturated, 3 to 8-membered, more preferably 5 or 6-membered heteromonocyclic group containing 1 to 2 oxygen atom(s) and 1 to 3 nitrogen atom(s), for example, morpholinyl, [e.g. morpholino, 2-morpholinyl and 3-morpholinyl], sydnonyl, etc.;

unsaturated, condensed heterocyclic group containing 1 to 2 oxygen atom(s) and 1 to 3 nitrogen atom(s), for example, benzoxazolyl, benzoxadiazolyl, etc.;

unsaturated, 3 to 8-membered, more preferably 5 or 6-membered heteromonocyclic group containing 1 to 2 sulfur atom(s) and 1 to 3 nitrogen atom(s), for example, thiazolyl, [e.g. 2-thiazolyl, 4-thiazolyl, etc.], isothiazolyl [e.g. 3-thiazolyl, etc.], thiadiazolyl [e.g. 1,3,4-thiadiazol-2-yl, 1,2,4-thiadiazol-3-yl, etc.], thiazolinyl [e.g. 2-thiazolinyl, etc.];

unsaturated, condensed heterocyclic group containing 1 to 2 sulfur atom(s) and 1 to 3 nitrogen atom(s), for example, benzothiazolyl, benzothiadiazolyl, etc.;

unsaturated, 3 to 8-membered, preferably 5- or 6-membered heteromonocyclic group containing an oxygen atom, for example, furyl, etc.;

saturated, 3 to 8-membered, more preferably 5 or 6-membered heteromonocyclic group containing an oxygen atom, for example, tetrahydrofuryl, etc.; and the like.

The heterocyclic groups as mentioned above may have suitable substituent(s) such as halogen [e.g. fluorine, chlorine, bromine and iodine], lower alkyl, lower alkoxy, oxo, and the like, and suitable examples of such lower alkyl and lower alkoxy groups may be the same as those as exemplified before.

Suitable "di(lower)alkylamino" may be dimethylaminomethyl, dimethylaminoethyl, dimethylaminopropyl, or the like.

In the present invention, the preferred embodiment of the compound [I] can be represented by the following chemical formula:

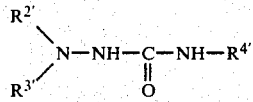

[I']

wherein
R$^{2'}$ and R$^{3'}$ are taken together with the attached nitrogen atom to form unsaturated 6-membered heterocyclic group optionally substituted with lower alkyl, more preferably 1,2,3,6-tetrahydropyridin-1-yl optionally substituted with C$_1$-C$_4$ alkyl [e.g. 1,2,3,6-tetrahydropyridin- 1-yl, 4-methyl-1,2,3,6-tetrahydropyridin-1-yl, 5-methyl-1,2,3,6-tetrahydropyridin-1-yl, etc.], or R$^{2'}$ and R$^{3'}$ are each lower alkenyl, more preferablly C$_2$-C$_4$ alkenyl [e.g. vinyl, allyl, 1-propenyl, etc.]; and
R$^{4'}$ is lower alkyl optionally substituted with di(-lower)alkylamino or a heterocyclic group, more preferably C$_1$-C$_4$ alkyl optionally substituted with di(C$_1$-C$_4$) alkylamino or pyridyl [e.g. methyl, ethyl, propyl, butyl, t-butyl, dimethylaminomethyl, 1- or 2-dimethylaminoethyl, 1- or 2- or 3-dimethylaminopropyl, 2- or 3- or 4-pyridylmethyl, etc.], or heterocyclic group optionally having halogen, lower alkyl or lower alkoxy, more preferably pyridyl optionally having halogen, C$_1$-C$_4$ alkyl or C$_1$-C$_4$ alkoxy [e.g. 2- or 3- or 4-pyridyl, 2-chloropyridin-5-yl, 6-methylpyridin-2-yl, 3-methylpyridin-2-yl, 4-methylpyridin-2-yl, 2-methoxypyridin-5-yl, etc.], pyrimidinyl [e.g. 2- or 4-pyrimidinyl, etc.], pyrazinyl, thiazolyl [e.g. 2- or 4- or 5-thiazolyl, etc.], thiazolinyl [e.g. 2-thiazolinyl, etc.], benzothiazolyl [e.g. 2-benzothiazolyl, etc.], 1,2,3,6,-tetrahydropyridin-1-yl, pyrazolyl [e.g. 3-pyrazolyl, etc.], pyrrolidinyl [e.g. 1-pyrrolidinyl, etc.], morpholinyl [e.g. morpholino, etc.], tetrahydrofuryl substituted with oxo [e.g. 2-oxotetrahydrofuran-3-yl, etc.].

Suitable pharmaceutically acceptable salt of the object compound [I] is conventional non-toxic salt and includes an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an acidic amino acid [e.g. aspartic acid salt, glutamic acid salt, etc.], and the like.

With respect to the salts of the compounds [Ia], [Ib], [Ic] and [Id] in the Processes 1 to 5, it is to be noted that these compounds are included within the scope of the compound [I], and accordingly the suitable examples of the salts of these compounds are to be referred to those as exemplified for the object compound [I].

The processes for preparing the compound [I] and its salts are explained in detail in the following.

Process 1

The compound [Ia] and its salt can be prepared by reacting a compound [II] or its salt with a compound [III] or its salt.

Suitable salts of the compounds [II] and [III] may be the same as those exemplified for the compound [I].

This reaction is usually carried out in a solvent such as water, methanol, ethanol, dioxane, tetrahydrofuran, benzene, chloroform, methylene chloride or any other organic solvent which does not adversely influence the reaction.

Further, this reaction can be carried out in the presence of an inorganic or organic base such as an alkali metal bicarbonate [e.g. sodium bicarbonate, potassium bicarbonate, etc.], alkali metal carbonate [e.g. sodium carbonate, potassium carbonate, etc.], alkaline earth metal carbonate [e.g. magnesium carbonate, calcium carbonate, etc.], tri(lower)alkylamine [e.g. trimethylamine, triethylamine, N,N-diisopropyl-N-ethylamine, etc.], pyridine compounds [e.g. pyridine, picoline, lutidine, N,N-di(lower)alkylaminopyridine such as 4-(N,N-dimethylamino)pyridine, etc.], quinoline, N-lower alkylmorphorine [e.g. N-methylmorphorine, etc.], N,N-di(lower)alkylbenzylamine [e.g. N,N-dimethylbenzylamine, etc.], and the like.

The reaction temperature is not critical, and the reaction is usually carried out under cooling to warming.

Process 2

The compound [I] and its salt can be prepared by reacting a compound [II] or its salt with a compound [IV] or its reactive derivative at the carboxy or hydroxy thiocarbonyl group or a salt thereof.

Suitable salts of the compound [II] may be the same as those exemplified for the compounds [I].

Suitable reactive derivative at the carboxy or hydroxy thiocarbonyl group of the compound [IV] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as substituted or unsubstituted lower alkyl ester [e.g. methyl ester, ethyl ester, propyl ester, hexyl ester, trichloromethyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like. These reactive derivatives can be optionally selected according to the kind of the compound [IV] to be used.

Suitable salts of the compound [IV] and its reactive derivative may include an acid addition salt exemplified for the compounds[I] and a conventional base salt such as an organic base salt [e.g. trimethylamine salt, triethylamine salt, pyridine salt, picoline salt, dicyclohexylamine salt, N,N'-dibenzylethylenediamine salt, etc.], an ammonium salt, an alkali metal salt [e.g. sodium salt, potassium salt, etc.], an alkaline earth metal salt [e.g. calcium salt, magnesium salt, etc.] and the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound [IV] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction temperature is not critical, and the reaction can be carried out under cooling to heating.

Process 3

The compound [I] and its salt can be prepared by reacting a compound [V] or its reactive derivative at the carboxy or hydroxy thiocarbonyl group or a salt thereof with a compound [VI] or the salt.

Suitable reactive derivatives at the carboxy or hydroxy thiocarbonyl group of the compound [V] and suitable salts of the compound [V] and its reactive derivative may be the same as those exemplified for the compound [IV] in the above Process 2.

Suitable salts of the compound [VI] may be the same as those exemplified for the compounds [I].

This reaction can be carried out in substantially the same manner as Process 2, and therefore the reaction mode and reaction conditions [e.g. solvent, condensing agent, reaction temperature, etc.] of this reaction are to be referred to those as explained in Process 2.

Process 4

The compound [Ib] and its salt can be prepared by reducing a compound [VII] or its salt.

The reaction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, etc. or a mixture thereof.

The reaction is preferably carried out under somewhat milder conditions such as under cooling to warming.

In this process, the pyridinio moiety of the compound [VII] is reduced to piperidino, 1,4-dihydropyridin-1-yl, 1,2-dihydropyridin-1-yl or 1,2,3,6-tetrahydropyridin-1-yl group according to the reducing method and the reagent to be used in this process.

Process 5

The compound [Id] and its salt can be prepared by reducing a compound [Ic] or its salt.

This reaction can be carried out in substantially the same manner as Process 4, and therefore the reaction mode and reaction conditions [e.g. reduction method, reducing agent, solvent, reaction temperature, etc.] of this reaction are to be referred to those as explained in Process 4.

The compounds [I], [Ia], [Ib] and [Id] obtained by the above processes are isolated and purified by a conventional method such as pulverization, recrystallization, column chromatography, reprecipitation or the like.

It is to be noted that each of the object compound [I] and the starting compounds [II], [III], [IV], [V], [VI] and [VII] may include one or more stereoisomers due to asymmetric carbon atom(s) and/or carbon and carbon double bond (i.e. Z-isomer and E-isomer), and all of such isomers and mixture thereof are included within the scope of this invention.

Among the starting compounds [IV], [V] and [VII], some of them are new and such compounds can be prepared by the methods of Preparations mentioned later and any process known in the art for preparing structurally analogous compounds thereto.

The new semicarbazide derivatives [I] and a pharmaceutically acceptable salt thereof possess antiinflammatory and analgesic activities, and are useful for a therapeutic treatment of inflammation and various pains [e.g. headache, toothache, menorrhalgia, etc.].

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating inflammation and various pains. In general, amounts between 0.1 mg/body and about 1,000 mg/body may be administered per day.

In order to illustrate the usefulness of the object compound [I], the pharmacological test data of the representative compound [I] are shown in the following.

Test Compounds

N-[(4-Pyridylcarbamoyl)amino]-1,2,3,6-tetrahydropyridine (hereinafter referred to as Compound A)
N-[(3-Pyridylcarbamoyl)amino]-1,2,3,6-tetrahydropyridine (hereinafter referred to as Compound B)
N-[(2-Pyridylcarbamoyl)amino]-1,2,3,6-tetrahydropyridine (hereinafter referred to as Compound C)
N-[(4-Pyrimidinylcarbamoyl)amino]-1,2,3,6-tetrahydropyridine (hereinafter referred to as Compound D)
N-(Pyrazinylcarbamoylamino)-1,2,3,6-tetrahydropyridine (hereinafter referred to as Compound E)
N-[[(2-Chloropyridin-5-yl)carbamoyl]amino]-1,2,3,6-tetrahydropyridine (hereinafter referred to as Compound F)
N-[(1-Pyrrolidinylcarbamoyl)amino]-1,2,3,6-tetrahydropyridine (hereinafter referred to as Compound G)
N,N'-[Bis-(1,2,3,6-tetrahydropyridin-1-yl)]urea (hereinafter referred to as Compound H)

Test A (ANTIINFLAMMATORY ACTIVITY)

(1) Carrageenin Foot Edema (i) Test Method:

Five male Sprague-Dawley rats weighing about 200 g were used per group.

Paw edema was induced by subplantar injection of 1% carrageenin (0.1 ml/rat) into the right hind paw. The test drug was suspended in 0.5% methylcellulose and administered orally 60 minutes before phlogogen. Paw volume was measured with plethysmometer (Ugo Bazil Co., Ltd.) by water displacement immersing the paw to the lateral malleolus. The difference of paw volume before and 3 hours after the phlogogen was designated as edema volume.

The data were analyzed statistically by student's t-test.

(ii) Test Results:

| Compound | Inhibition (%) (Dose: 32 mg/kg) |
|---|---|
| A | 41.4 |
| B | 45.9 |
| C | 50.9 |
| D | 48.0 |
| E | 54.7 |
| F | 49.9 |

Test B (ANALGESIC ACTIVITY)

(1) Acetic Acid Induced Writhing (i) Test Method

Ten male ddY strain mice were used per group. To estimate the frequency of writhing syndrome, the animals were observed from 3 to 13 minutes after an intraperitoneal injection of 0.2 ml/10 g of 0.6% acetic acid. The drugs were given orally 60 minutes before acetic acid. The frequency of writhing syndrome in the treated animals was compared with that in the non-treated control animals.

(ii) Test Results:

| Compound | Inhibition (%) (Dose: 32 mg/kg) |
|---|---|
| A | 73.4 |
| B | 95.5 |
| D | 68.5 |
| F | 75.1 |
| G | 84.7 |
| H | 82.0 |

The following Preparations and Examples are given for the purpose of illustrating the present invention in more detail.

PREPARATION 1

To a solution of N-amino-1,2,3,6-tetrahydropyridine hydrochloride (1.346 g) and triethylamine (2.024 g) in methylene chloride (60 ml) was added a solution of phenyl chloroformate (1.566 g) in methylene chloride (40 ml) and the mixture was stirred for 4 hours at 5° C. Evaporation of the solvent gave a residue, which was extracted with ethyl acetate (150 ml). The extract was washed with water and dried over magnesium sulfate. The solvent was evaporated in vacuo to give N-(phenoxycarbonylamino)-1,2,3,6-tetrahydropyridine (2.01 g), which was recrystallized from diisopropyl ether to give the desired compound (0.732 g) as colorless needles.

mp: 124°–125.5° C.
IR (Nujol): 3230, 1720, 1600, 1540 cm$^{-1}$.
NMR (CDCl$_3$, δ): 2.30 (2H, m), 3.06 (2H, t, J=6 Hz), 3.47 (2H, m), 5.69 (2H, m), 6.33 (1H, s), 7.10–7.47 (5H, m).
Elemental Analysis: Calcd. for $C_{12}H_{14}N_2O_2$: Calcd.: C 66.04, H 6.47, N 12.84. Found: C 66.28, H 6.44, N 13.08.

The following compounds (Preparations 2 to 9) were obtained according to a similar manner to that of Preparation 1.

PREPARATION 2

4-(Phenoxycarbonylamino)pyridine

IR (Nujol): 1760, 1630, 1600, 1550 cm$^{-1}$.
NMR (CDCl$_3$, δ): 7.10–7.60 (7H, m), 8.50–8.57 (2H, m), 9.17 (1H, s).

PREPARATION 3

2-(Phenoxycarbonylamino)pyridine mp: 149°–150° C.
IR (Nujol): 3200, 1745, 1610, 1590 cm$^{-1}$.
NMR (CDCl$_3$, δ): 6.9–8.6 (9H, m), 10.66 (1H, s).

PREPARATION 4

2-(Phenoxycarbonylamino)pyrimidine mp: 131°–132° C.
IR (Nujol): 1770, 1445 cm$^{-1}$.

NMR (CDCl$_3$, δ): 7.06 (1H, m), 7.18–7.66 (5H, m), 8.76 (2H, d, J=3 Hz), 11.04 (1H, s).

PREPARATION 5

2-(Phenoxycarbonylamino)thiazole mp: 185°–185.5° C.
IR (Nujol): 1735, 1460 cm$^{-1}$.

PREPARATION 6

2-Chloro-5-(phenoxycarbonylamino)pyridine mp: 142.5°–144° C.
IR (Nujol): 1745, 1460 cm$^{-1}$.
NMR (CDCl$_3$, δ): 7.00–7.56 (6H, m), 7.96 (1H, dd, J=9 Hz, 3 Hz), 8.34 (1H, d, J=3 Hz).

PREPARATION 7

2-Methoxy-5-(phenoxycarbonylamino)pyridine mp: 117°–118° C.
IR (Nujol): 3230, 1735, 1460 cm$^{-1}$.
NMR (CDCl$_3$, δ): 3.88 (3H, s), 6.64 (1H, d, J=9 Hz), 7.01–7.48 (6H, m), 7.71 (1H, dd, J=9 Hz, 2.5 Hz), 8.08 (1H, d, J=2.5 Hz).

PREPARATION 8

N-(Phenoxycarbonylamino)pyrrolidine mp: 133.5°–134° C.
IR (Nujol): 3200, 1720, 1460 cm$^{-1}$.
NMR (CDCl$_3$, δ): 1.86 (4H, m), 2.98 (4H, m), 6.01 (1H, s), 6.98–7.58 (5H, m).

PREPARATION 9

N-(Phenoxycarbonylamino)morpholine mp: 143°–144° C.
IR (Nujol): 3210, 1710 cm$^{-1}$.
NMR (CDCl$_3$, δ): 2.88 (4H, t, J=5 Hz), 3.77 (4H, t, J=5 Hz), 6.07 (1H, s), 7.02–7.48 (5H, m).

EXAMPLE 1

To a solution of tert-butyl isocyanate (0.991 g) in methylene chloride (8 ml) was added dropwise to a mixture of N-amino-1,2,3,6-tetrahydropyridine hydrochloride (1.346 g) and triethylamine (1.012 g) in methylene chloride (40 ml) under ice bath cooling. The mixture was stirred for an hour at about 5° C. The reaction mixture was evaporated to dryness, and then the residue was dissolved in ethyl acetate (50 ml). The solution was washed with water (40 ml), dried over magnesium sulfate and evaporated to dryness. The crude residue was washed with ether and dried to give N-[(tert-butylcarbamoyl)amino]-1,2,3,6-tetrahydropyridine (0.50 g).

mp: 155.5°–156.5° C.
IR (Nujol): 3350, 3200, 3100, 1675 cm$^{-1}$.
NMR (CDCl$_3$, δ): 1.35 (9H, s), 2.27 (2H, m), 2.85 (2H, t, J=7 Hz), 3.23 (2H, m), 5.27 (1H, s), 5.67 (2H, m), 6.03 (1H, br s).

The following compounds (Examples 2 to 25) were obtained according to a similar manner to that of Example 1.

EXAMPLE 2

N-[(4-Pyridylcarbamoyl)amino]-1,2,3,6-tetrahydropyridine mp: 185°–187° C.
IR (Nujol) : 3200, 3100, 1680, 1580 cm$^{-1}$.
NMR (CDCl$_3$, δ): 2.10–2.60 (2H, m), 2.70–3.30 (2H, m), 3.10–3.60 (2H, m), 5.74 (2H, br s), 6.54 (1H, s), 7.30–7.60 (2H, m), 8.30–8.60 (2H, m).

EXAMPLE 3

N-[(3-Pyridylcarbamoyl)amino]-1,2,3,6-tetrahydropyridine mp: 163°–166° C.
IR (Nujol): 3180, 3070, 1667, 1578, 1520–1530 cm$^{-1}$.
NMR (CD$_3$OD, δ): 2.20–2.60 (2H, m), 2.98 (2H, t, J=6 Hz), 5.72 (2H, s), 7.30–7.50 (1H, m), 7.90–8.30 (2H, m), 8.69 (1H, d, J=2.5 Hz).

EXAMPLE 4

N-[(2-Pyridylcarbamoyl)amino]-1,2,3,6-tetrahydropyridine mp: 163°–164.5° C.
IR (Nujol): 3300, 3200, 3100, 1685, 1650 cm$^{-1}$.
NMR (CDCl$_3$, δ): 2.33 (2H, m), 2.97 (2H, m), 3.38 (2H, m), 5.70 (2H, m), 6.35 (1H, s), 6.83–8.28 (4H, m), 8.80 (1H, s).

EXAMPLE 5

N-[[(2-Chloropyridin-5-yl)carbamoyl]amino]-1,2,3,6-tetrahydropyridine mp: 173°–174° C.
IR (Nujol): 3210, 1670, 1460 cm$^{-1}$.
NMR (CDCl$_3$, δ): 2.35 (2H, m), 2.98 (2H, m), 3.36 (2H, m), 5.70 (2H, m), 6.45 (1H, s), 7.20 (1H, d, J=8 Hz), 7.97–8.46 (3H, m).

EXAMPLE 6

N-[[(2-Methoxypyridin-5-yl)carbamoyl]amino]-1,2,3,6-tetrahydropyridine mp: 164°–164.5° C.
IR (Nujol): 3350, 1680, 1460 cm$^{-1}$.
NMR (CDCl$_3$, δ): 2.33 (2H, m), 2.98 (2H, m), 3.37 (2H, m), 3.90 (3H, s), 5.73 (2H, m), 6.30 (1H, s), 6.73 (1H, d, J=6 Hz), 7.87 (1H, dd, J=6 Hz, 2 Hz), 8.05 (1H, s), 8.18 (1H, d, J=2 Hz).

EXAMPLE 7

N-[(2-Pyrimidinylcarbamoyl)amino]-1,2,3,6-tetrahydropyridine mp: 202°–203° C.
IR (Nujol): 1690 cm$^{-1}$.
NMR (CDCl$_3$, δ): 2.37 (2H, m), 3.18 (2H, m), 3.57 (2H, m), 5.77 (2H, m), 6.96 (1H, t, J=5 Hz), 8.65 (2H, d, J=5 Hz), 9.50 (1H, s), 10.16 (1H, s).

EXAMPLE 8

N-[(4-Pyrimidinylcarbamoyl)amino]-1,2,3,6-tetrahydropyridine mp: 187.5°–188° C.
IR (Nujol): 1707, 1500, 1460 cm$^{-1}$.
NMR (CDCl$_3$, δ): 2.10–2.66 (2H, m), 2.60–3.74 (4H, m), 5.60–5.86 (2H, m), 6.14–6.60 (1H, m), 8.08 (1H, d, J=6 Hz), 8.55 (1H, d, J=6 Hz), 8.80 (1H, s), 8.68–9.10 (1H, m).

EXAMPLE 9

N-(Pyrazinylcarbamoylamino)-1,2,3,6-tetrahydropyridine mp: 154°–155° C.
IR (Nujol): 1690, 1515, 1415 cm$^{-1}$.

NMR (CDCl₃, δ): 2.04–2.68 (2H, m), 2.68–3.19 (2H, m), 3.19–3.68 (2H, m), 5.56–5.86 (2H, m), 6.36–6.74 (1H, m), 8.05–8.36 (2H, m), 8.66–9.00 (1H, m), 9.46 (1H, s).

EXAMPLE 10

N-[(2-Thiazolylcarbamoyl)amino]-1,2,3,6-tetrahydropyridine mp: 171°–172° C.

IR (Nujol) : 3320, 3180, 3100, 1700, 1520 cm⁻¹.

NMR (CDCl₃, δ): 2.42 (2H, m), 3.06 (2H, m), 3.43 (2H, m), 5.78 (2H, m), 6.97 (1H, m), 7.26–7.66 (2H, m), 9.74 (1H, s).

EXAMPLE 11

N-[(2-Thiazolinylcarbamcyl)amino]-1,2,3,6-tetrahydropyridine mp: 137.5°–138° C.

IR (Nujol): 1710, 1610 cm⁻¹.

NMR (CDCl₃, δ): 2.00–2.47 (2H, m), 2.78–3.14 (2H, m), 3.16–3.48 (4H, m), 3.65–4.16 (2H, m), 5.50–5.82 (2H, m), 6.11–6.58 (1H, m), 8.62–9.04 (1H, m).

EXAMPLE 12

N-[(2-Benzothiazolylcarbamoyl)amino]-1,2,3,6-tetrahydropyridine mp: >250° C.

IR (Nujol) : 3340, 1710, 1535 cm⁻¹.

NMR (DMSO-d₆, δ): 2.00–2.66 (2H, m), 2.66–3.10 (2H, m), 3.10–3.53 (2H, m), 5.55–5.83 (2H, m), 7.04–8.03 (4H, m), 8.52 (1H, s), 10.14 (1H, s).

EXAMPLE 13

N,N'-[Bis-(1,2,3,6-tetrahydropyridin-1-yl)]urea mp: 172°–173.5° C.

IR (Nujol): 3240, 1670 cm⁻¹.

NMR (CDCl₃, δ): 2.12–2.53 (4H, m), 2.84 (4H, t, J=6 Hz), 3.21–3.50 (2H, m), 5.51–5.70 (2H, m), 6.34 (2H, s).

EXAMPLE 14

N-[(3-Pyrazolylcarbamoyl)amino]-1,2,3,6-tetrahydropyridine mp: 154°–156° C.

IR (Nujol): 3250, 2950, 1660, 1565 cm⁻¹.

NMR (DMSO-d₆, δ): 2.01–2.40 (2H, m), 2.86 (2H, t, J=6 Hz), 3.12–3.50 (2H, m), 5.53–5.80 (2H, m), 6.28 (1H, d, J=2 Hz), 7.44 (1H, d, J=2 Hz), 7.60 (1H, s), 8.43 (1H, s), 12.11 (1H, s).

EXAMPLE 15

N-[(1-Pyrrolidinylcarbamoyl)amino]-1,2,3,6-tetrahydropyridine mp: 182.5°–183° C.

IR (Nujol) : 1665, 1460 cm⁻¹.

NMR (CDCl₃, δ): 1.81 (4H, m), 2.30 (2H, m), 2.62–3.10 (6H, m), 3.30 (2H, m), 5.67 (2H, m), 6.04–6.56 (2H, m).

EXAMPLE 16

N-[(Morpholinocarbamoyl)amino]-1,2,3,6-tetrahydropyridine mp: 204.5°–205° C.

IR (Nujol): 3230, 1660, 1495, 1460 cm⁻¹.

NMR (CDCl₃, δ): 2.00–2.43 (2H, m), 2.53–3.10 (6H, m), 3.16–3.47 (2H, m), 3.62–3.94 (4H, m), 5.53–5.78 (2H, m), 5.98–6.33 (1H, m), 6.35–6.64 (1H, m).

EXAMPLE 17

N-[[(2-Oxotetrahydrofuran-3-yl)carbamoyl]amino]-1,2,3,6-tetrahydropyridine mp: 202°–203.5° C.

IR (Nujol): 3350, 1770, 1670, 1530 cm⁻¹.

NMR (DMSO-d₆, δ): 1.96–2.39 (3H, m), 2.62–2.88 (2H, m), 3.03–3.31 (3H, m), 4.02–4.60 (3H, m), 5.54–5.72 (2H, m), 6.96 (1H, d, J=7 Hz), 7.30 (1H, s).

EXAMPLE 18

N-[(4-Pyridylmethylcarbamoyl)amino]-1,2,3,6-tetrahydropyridine mp: 183°–183.5° C.

IR (Nujol): 1660, 1535 cm⁻¹.

NMR (CDCl₃, δ): 2.00–2.53 (2H, m), 2.68–3.11 (2H, m), 3.11–3.48 (2H, m), 4.46 (2H, d, J=6 Hz), 5.53–5.83 (2H, m), 5.83–6.08 (1H, m), 6.34–6.76 (1H, m), 7.09–7.32 (2H, m), 8.38–8.64 (2H, m).

EXAMPLE 19

N-[(4-Pyridylcarbamoyl)amino]-4-methyl-1,2,3,6-tetrahydropyridine mp: 164.5°–166° C.

IR (Nujol): 3190, 3090, 1685 cm⁻¹.

NMR (CDCl₃, δ): 1.78 (3H, s), 2.01–2.49 (2H, m), 2.67–3.20 (2H, m), 3.20–3.67 (2H, m), 5.23–5.55 (2H, m), 6.54 (1H, s), 7.45 (2H, d, J=5.5 Hz), 8.22–8.68 (3H, m).

EXAMPLE 20

N-[[(6-Methylpyridin-2-yl)carbamoyl]amino]-1,2,3,6-tetrahydropyridine mp: 145.5°–147° C.

IR (Nujol): 3340, 1720 cm⁻¹.

NMR (CDCl₃, δ): 2.03–2.61 (2H, m), 2.41 (3H, s), 2.72–3.12 (2H, m), 3.12–3.68 (2H, m), 5.55–5.81 (2H, m), 6.10–6.60 (1H, m), 6.75 (1H, d, J=7 Hz), 7.21–7.96 (2H, m), 8.37–8.88 (1H, s).

EXAMPLE 21

N-[[3-(Dimethylamino)propylcarbamoyl]amino]-1,2,3,6-tetrahydropyridine mp: 86°–88° C.

IR (Nujol): 3400, 1640 cm⁻¹.

EXAMPLE 22

N-[(4-Pyridylcarbamoyl)amino]-5-methyl-1,2,3,6-tetrahydropyridine mp: 169.0°–171.0° C.

IR (Nujol): 3170, 3080, 1675 cm⁻¹.

NMR (CDCl₃, δ): 1.65 (3H, s), 2.10–2.48 (2H, m), 2.51–3.63 (4H, m), 5.38–5.57 (1H, m), 6.44 (1H, s), 7.43 (2H, dd, J=7 Hz, 2 Hz), 8.26–8.55 (3H, m).

EXAMPLE 23

1,1-Diallyl-4-(4-pyridyl)semicarbazide mp: 85.5°–86.5° C.

IR (Nujol): 3240, 1680 cm⁻¹.

NMR (CDCl₃, δ): 3.37 (4H, d, J=5 Hz), 5.11–5.44 (4H, m), 5.63–6.14 (2H, m), 6.43 (1H, s), 7.40 (2H, dd, J=7 Hz, 2 Hz), 8.26 (1H, s), 8.42 (2H, dd, J=7 Hz, 2 Hz).

EXAMPLE 24

N-[[(4-Methylpyridin-2-yl)carbamoyl]amino]-1,2,3,6-tetrahydropyridine mp: 163.5°–165° C.
IR (Nujol): 3320, 3190, 1680 cm$^{-1}$.
NMR (CDCl$_3$, δ): 2.14–2.48 (5H, m), 2.70–3.11 (2H, m), 3.16–3.62 (2H, m), 5.56–5.79 (2H, m), 6.30 (1H, s), 6.76 (1H, d, J=6 Hz), 7.93 (1H, s), 8.08 (1H, d, J=6 Hz), 8.75 (1H, s).

EXAMPLE 25

N-[[(3-Methylpyridin-2-yl)carbamoyl]amino]-1,2,3,6-tetrahydropyridine mp: 135.0°–137.0° C.
IR (Nujol): 3220, 1675 cm$^{-1}$.
NMR (CDCl$_3$, δ): 2.00–2.54 (5H ,m), 2.78–3.66 (4H, m), 5.55–5.86 (2H, m), 6.65–7.08 (2H, m), 7.22–7.61 (2H, m), 7.96–8.30 (1H, m).

EXAMPLE 26

A solution of 4-(phenoxycarbonylamino)pyridine (4.284 g), N-amino-1,2,3,6-tetrahydropyridine hydrochloride (4.038 g) and triethylamine (3.036 g) in chloroform (70 ml) was refluxed for 20 hours. After evaporation of chloroform, the residue was extracted with ethyl acetate (200 ml). The extract was washed with water, dried over magnesium sulfate and evaporated in vacuo. The residue was chromatographed on silica gel (52 g) using chloroform to give N-[(4-pyridylcarbamoyl)amino]-1,2,3,6-tetrahydropyridine (2.005 g).

mp: 185°–187° C.
IR (Nujol): 3200, 3100, 1680, 1580 cm$^{-1}$.
NMR (CDCl$_3$, δ): 2.10–2.60 (2H, m), 2.70–3.30 (2H, m), 3.10–3.60 (2H, m), 5.74 (2H, br s), 6.54 (1H, s), 7.30–7.60 (2H, m), 8.30–8.60 (12H, m).

The following compounds (Examples 27 to 49) were obtained according to a similar manner to that of Example 26.

EXAMPLE 27

N-[(2-Pyridylcarbamoyl)amino]-1,2,3,6-tetrahydropyridine mp: 163°–164.5° C.
IR (Nujol): 3300, 3200, 3100, 1685, 1650 cm$^{-1}$.
NMR (CDCl$_3$, δ): 2.33 (2H, m), 2.97 (2H, m), 3.38 (2H, m), 5.70 (2H, m), 6.35 (1H, s), 6.83–8.28 (4H, m), 8.80 (1H, s).

EXAMPLE 28

N-[(2-Pyrimidinylcarbamoyl)amino]-1,2,3,6-tetrahydropyridine mp: 202°–203° C.
IR (Nujol): 1690 cm$^{-1}$.
NMR (CDCl$_3$, δ): 2.37 (2H, m), 3.18 (2H, m), 3.57 (2H, m), 5.77 (2H, m), 6.96 (1H, t, J=5 Hz), 8.65 (2H, d, J=5 Hz), 9.50 (1H, s), 10.16 (1H, s).

EXAMPLE 29

N-[(2-Thiazolylcarbamoyl)amino]-1,2,3,6-tetrahydropyridine mp: 171°–172° C.
IR (Nujol): 3320, 3180, 3100, 1700, 1520 cm$^{-1}$.
NMR (CDCl$_3$, δ): 2.42 (2H, m), 3.06 (2H, m), 3.43 (2H, m), 5.78 (2H, m), 6.97 (1H, m), 7.26–7.66 (2H, m), 9.74 (1H, s).

EXAMPLE 30

N-[[(2-Chloropyridin-5-yl)carbamoyl]amino]-1,2,3,6-tetrahydropyridine mp: 173°–174° C.
IR (Nujol): 3210, 1670, 1460 cm$^{-1}$.
NMR (CDCl$_3$, δ): 2.35 (2H, m), 2.98 (2H, m), 3.36 (2H, m), 5.70 (2H, m), 6.45 (1H, s), 7.20 (1H, d, J=8 Hz), 7.97–8.46 (3H, m).

EXAMPLE 31

N-[[(2-Methoxypyridin-5-yl)carbamoyl]amino]-1,2,3,6-tetrahydropyridine mp: 164°–164.5° C.
IR (Nujol): 3350, 1680, 1460 cm$^{-1}$.
NMR (CDCl$_3$, δ): 2.33 (2H, m), 2.98 (2H, m), 3.37 (2H, m), 3.90 (3H, s), 5.73 (2H, m), 6.30 (1H, s), 6.73 (1H, d, J=6 Hz), 7.87 (1H, dd, J=6 Hz, 2 Hz), 8.05 (1H, s), 8.18 (1H, d, J=2 Hz).

EXAMPLE 32

N-[(1-Pyrrolidinylcarbamoyl)amino]-1,2,3,6-tetrahydropyridine mp: 182.5°–183° C.
IR (Nujol): 1665, 1460 cm$^{-1}$.
NMR (CDCl$_3$, δ): 1.81 (4H, m), 2.30 (2H, m), 2.62–3.10 (6H, m), 3.30 (2H, m), 5.67 (2H, m), 6.04–6.56 (2H, m).

EXAMPLE 33

N-[(Morpholinocarbamoyl)amino]-1,2,3,6-tetrahydropyridine mp: 204.5°–205° C.
IR (Nujol): 3230, 1660, 1495, 1460 cm$^{-1}$.
NMR (CDCl$_3$, δ): 2.00–2.43 (2H, m), 2.53–3.10 (6H, m), 3.16–3.47 (2H, m), 3.62–3.94 (4H, m), 5.53–5.78 (2H, m), 5.98–6.33 (1H, m), 6.35–6.64 (1H, m).

EXAMPLE 34

N-[(tert-Butylcarbamoyl)amino]-1,2,3,6-tetrahydropyridine mp: 155.5°–156.5° C.
IR (Nujol): 3350, 3200, 3100, 1675 cm$^{-1}$.
NMR (CDCl$_3$, δ): 1.35 (9H, s), 2.27 (2H, m), 2.85 (2H, t, J=7 Hz), 3.23 (2H, m), 5.27 (1H, s), 5.67 (2H, m), 6.03 (1H, br s).

EXAMPLE 35

N-[(4-Pyrimidinylcarbamoyl)amino]-1,2,3,6-tetrahydropyridine mp: 187.5°–188° C.
IR (Nujol): 1707, 1500, 1460 cm$^{-1}$.
NMR (CDCl$_3$, δ): 2.10–2.66 (2H, m), 2.60–3.74 (4H, m), 5.60–5.86 (2H, m), 6.14–6.60 (1H, m), 8.08 (1H, d, J=6 Hz), 8.55 (1H, d, J=6 Hz), 8.80 (1H, s), 8.68–9.10 (1H m).

EXAMPLE 36

N-(Pyrazinylcarbamoylamino)-1,2,3,6-tetrahydropyridine mp: 154°–155° C.
IR (Nujol): 1690, 1515, 1415 cm$^{-1}$.
NMR (CDCl$_3$, δ): 2.04–2.68 (2H, m), 2.68–3.19 (2H, m), 3.19–3.68 (2H, m), 5.56–5.86 (2H, m), 6.36–6.74 (1H, m), 8.05–8.36 (2H, m), 8.66–9.00 (1H, m), 9.46 (1H, s).

EXAMPLE 37

N-[(2-Thiazolinylcarbamoyl)amino]-1,2,3,6-tetrahydropyridine mp: 137.5°–138° C.
IR (Nujol): 1710, 1610 cm$^{-1}$.
NMR (CDCl$_3$, δ): 2.00–2.47 (2H, m), 2.78–3.14 (2H, m), 3.16–3.48 (4H, m), 3.65–4.16 (2H, m), 5.50–5.82 (2H, m), 6.11–6.58 (1H, m), 8.62–9.04 (1H, m).

EXAMPLE 38

N-[(2-Benzothiazolylcarbamoyl)amino]-1,2,3,6-tetrahydropyridine mp: >250° C.
IR (Nujol): 3340, 1710, 1535 cm$^{-1}$.
NMR (DMSO-d$_6$, δ): 2.00–2.66 (2H, m), 2.66–3.10 (2H, m), 3.10–3.53 (2H, m), 5.55–5.83 (2H, m), 7.04–8.03 (4H, m), 8.52 (1H, s), 10.14 (1H, s).

EXAMPLE 39

N,N'-[Bis-(1,2,3,6-tetrahydropyridin-1-yl)]urea mp: 172°–173.5° C.
IR (Nujol): 3240, 1670 cm$^{-1}$.
NMR (CDCl$_3$, δ): 2.12–2.53 (4H, m), 2.84 (4H, t, J=6 Hz), 3.21–3.50 (2H, m), 5.51–5.70 (2H, m) 6.34 (2H, s).

EXAMPLE 40

N-[(3-Pyrazolylcarbamoyl)amino]-1,2,3,6-tetrahydropyridine mp: 154°–156° C.
IR (Nujol): 3250, 2950, 1660, 1565 cm$^{-1}$.
NMR (DMSO-d$_6$, δ): 2.01–2.40 (2H, m), 2.86 (2H, t, J=6 Hz), 3.12–3.50 (2H, m), 5.53–5.80 (2H, m), 6.28 (1H, d, J=2 Hz), 7.44 (1H, d, J=2 Hz), 7.60 (1H, s), 8.43 (1H, s), 12.11 (1H, s).

EXAMPLE 41

N-[[(2-Oxotetrahydrofuran-3-yl)carbamoyl]amino]-1,2,3,6-tetrahydropyridine mp: 202°–203.5° C.
IR (Nujol): 3350, 1770, 1670, 1530 cm$^{-1}$.
NMR (DMSO-d$_6$, δ): 1.96–2.39 (3H, m), 2.62–2.88 (2H, m), 3.03–3.31 (3H, m), 4.02–4.60 (3H, m), 5.54–5.72 (2H, m), 6.96 (1H, d, J=7 Hz), 7.30 (1H, s).

EXAMPLE 42

N-[(4-Pyridylmethylcarbamoyl)amino]-1,2,3,6-tetrahydropyridine

IR (Nujol): 1660, 1535 cm$^{-1}$.
NMR (CDCl$_3$, δ): 2.00–2.53 (2H, m), 2.68–3.11 (2H, m), 3.11–3.48 (2H, m), 4.46 (2H, d, J=6 Hz), 5.53–5.83 (2H, m), 5.83–6.08 (1H, m), 6.34–6.76 (1H, m), 7.09–7.32 (2H, m), 8.38–8.64 (2H, m).

EXAMPLE 43

N-[(4-Pyridylcarbamoyl)amino]-4-methyl-1,2,3,6-tetrahydropyridine mp: 164.5°–166° C.
IR (Nujol): 3190, 3090, 1685 cm$^{-1}$.
NMR (CDCl$_3$, δ): 1.78 (3H, s), 2.01–2.49 (2H, m), 2.67–3.20 (2H, m), 3.20–3.67 (2H, m), 5.23–5.55 (2H, m), 6.54 (1H, s), 7.45 (2H, d, J=5.5 Hz), 8.22–8.68 (3H, m).

EXAMPLE 44

N-[[(6-Methylpyridin-2-yl)carbamoyl]amino]-1,2,3,6-tetrahydropyridine mp 145.5°–147° C.
IR (Nujol): 3340, 1720 cm$^{-1}$.
NMR (CDCl$_3$, δ): 2.03–2.61 (2H, m), 2.41 (3H, s), 2.72–3.12 (2H, m), 3.12–3.68 (2H, m), 5.55–5.81 (2H, m), 6.10–6.60 (1H, m), 6.75 (1H, d, J=7 Hz), 7.21–7.96 (2H, m), 8.37–8.88 (1H, s).

EXAMPLE 45

N-[[3-(Dimethylamino)propylcarbamoyl]amino]-1,2,3,6-tetrahydropyridine mp: 86°–88° C.
IR (Nujol): 3400, 1640 cm$^{-1}$.

EXAMPLE 46

N-[(4-Pyridylcarbamoyl)amino]-5-methyl-1,2,3,6-tetrahydropyridine mp: 169.0°–171.0° C.
IR (Nujol): 3170, 3080, 1675 cm$^{-1}$.
NMR (CDCl$_3$, δ): 1.65 (3H, s), 2.10–2.48 (2H, m), 2.51–3.63 (4H, m), 5.38–5.57 (1H, m), 6.44 (1H, s), 7.43 (2H, dd, J=7 Hz, 2 Hz), 8.26–8.55 (3H, m).

EXAMPLE 47

1,1-Diallyl-4-(4-pyridyl)semicarbazide mp: 85.5°–86.5° C.
IR (Nujol): 3240, 1680 cm$^{-1}$.
(CDCl$_3$, δ): 3.37 (4H, d, J=5 Hz), 5.11–5.44 (4H, m), 5.63–6.14 (2H, m), 6.43 (1H, s), 7.40 (2H, dd, J=7 Hz, 2 Hz), 8.26 (1H, s), 8.42 (2H, dd, J=7 Hz, 2 Hz).

EXAMPLE 48

N-[[(4-Methylpyridin-2-yl)carbamoyl]amino]-1,2,3,6-tetrahydropyridine mp: 163.5°–165° C.
IR (Nujol): 3320, 3190, 1680 cm$^{-1}$.
NMR (CDCl$_3$, δ): 2.14–2.48 (5H, m), 2.70–3.11 (2H, m), 3.16–3.62 (2H, m), 5.56–5.79 (2H, m), 6.30 (1H, s), 6.76 (1H, d, J=6 Hz), 7.93 (1H, s), 8.08 (1H, d, J=6 Hz), 8.75 (1H, s.

EXAMPLE 49

N-[[(3-Methylpyridin-2-yl)carbamoyl]amino]-1,2,3,6-tetrahydropyridine mp: 135.0°–137.0° C.
IR (Nujol): 3220, 1675 cm$^{-1}$.
NMR (CDCl$_3$, δ): 2.00–2.54 (5H, m), 2.78–3.66 (4H, m), 5.55–5.86 (2H, m), 6.65–7.08 (2H, m), 7.22–7.61 (2H, m), 7.96–8.30 (1H, m).

EXAMPLE 50

To a solution of trichloromethyl chloroformate (2.76 ml) in methylene chloride (200 ml) was added a solution of 3-aminopyridine (2.165 g) in methylene chloride (50 ml) and stirred for 2 hours at −50° C. The mixture was added to a mixture of N-amino-1,2,3,6-tetrahydropyridine hydrochloride (3.096 g) and triethylamine (2.327 g) in methylene chloride (100 ml) and the resultant mixture was stirred at the same temperature. After stirring for 1 hour, the reaction mixture was allowed to warm to ambient temperature and stirred for 17 hours. After evaporation of methylene chloride, the residue was dissolved in water (50 ml) and the resultant aqueous solution was adjusted to pH 8.0-8.5 with sodium bicarbonate. The precipitate was removed by filtration and the filtrate was extracted with ethyl acetate (300 ml). The extract was washed with water, dried over magnesium sulfate and evaporated in vacuo. The residue was chromatographed on silica gel (40 g) using chloroform. The fractions containing the desired compound were combined and concentrated under reduced pressure. The residue was recrystallized from ethyl acetate to give N-[(3-pyridylcarbamoyl)amino]-1,2,3,6-tetrahydropyridine (1.62 g).

mp: 163°-166° C.

IR (Nujol): 3180, 3070, 1667, 1578, 1520-1530 cm$^{-1}$.

NMR (CD$_3$OD, δ): 2.20-2.60 (2H, m), 2.98 (2H, t, J=6 Hz), 5.72 (2H, s), 7.30-7.50 (1H, m), 7.90-8.30 (2H, m), 8.69 (1H, d, J=2.5 Hz).

EXAMPLE 51

A mixture of N-(phenoxycarbonylamino)-1,2,3,6-tetrahydropyridine (2.61 g), 4-aminopyrimidine (0.95 g) and 4-dimethylaminopyridine (1.83 g) in 1,2-dichloroethane (80 ml) was refluxed for 2.5 hours. The reaction mixture was evaporated to dryness. The crude residue was dissolved in ethyl acetate (50 ml) and washed with water (50 ml), and then extracted with 5% hydrochloric acid (30 ml×2). The extract was neutralized with sodium bicarbonate and further extracted with chloroform (30 ml×2). The chloroform layer was washed with water (50 ml), dried over magnesium sulfate and evaporated to give N-[(4-pyrimidinylcarbamoyl)amino]-1,2,3,6-tetrahydropyridine (1.41 g), which was recrystallized from ethyl acetate.

mp: 187.5°-188° C.

IR (Nujol): 1707, 1500, 1460 cm$^{-1}$.

NMR (CDCl$_3$, δ): 2.10-2.60 (2H, m), 2.66-3.74 (4H, m), 5.60-5.86 (2H, m), 6.14-6.60 (1H, m), 8.08 (1H, d, J=6 Hz), 8.55 (1H, d, J=6 Hz), 8.80 (1H, s), 8.68-9.10 (1H, m).

The following compounds (Examples 52 to 75) were obtained according to a similar manner to that of Example 51.

EXAMPLE 52

N-(Pyrazinylcarbamoylamino)-1,2,3,6-tetrahydropyridine mp: 154°-155° C.

IR (Nujol) 1690, 1515, 1415 cm$^{-1}$.

NMR (CDCl$_3$, δ): 2.04-2.68 (2H, m), 2.68-3.19 (2H, m), 3.19-3.68 (2H, m), 5.56-5.86 (2H, m), 6.36-6.74 (1H, m), 8.05-8.36 (2H, m), 8.66-9.00 (1H, m), 9.46 (1H, s).

EXAMPLE 53

N-[(2-Thiazolinylcarbamoyl)amino]-1,2,3,6-tetrahydropyridine mp: 137.5°-138° C.

IR (Nujol): 1710, 1610 cm$^{-1}$.

NMR (CDCl$_3$, δ): 2.00-2.47 (2H, m), 2.78-3.14 (2H, m), 3.16-3.48 (4H, m), 3.65-4.16 (2H, m), 5.50-5.82 (2H, m), 6.11-6.58 (1H, m), 8.62-9.04 (1H, m).

EXAMPLE 54

N-[(4-Pyridylmethylcarbamoyl)amino]-1,2,3,6-tetrahydropyridine mp: 183°-183.5° C.

IR (Nujol): 1660, 1535 cm$^{-1}$.

NMR (CDCl$_3$, δ): 2.00-2.53 (2H, m), 2.68-3.11 (2H, m), 3.11-3.48 (2H, m), 4.46 (2H, d, J=6 Hz), 5.53-5.83 (2H, m), 5.83-6.08 (1H, m), 6.34-6.76 (1H, m), 7.09-7.32 (2H, m), 8.38-8.64 (2H, m)

EXAMPLE 55

N-[(2-Benzothiazolylcarbamoyl)amino]-1,2,3,6-tetrahydropyridine mp: >250° C.

IR (Nujol): 3340, 1710, 1535 cm$^{-1}$.

NMR (DMSO-d$_6$, δ): 2.00-2.66 (2H, m), 2.66-3.10 (2H, m), 3.10-3.53 (2H, m), 5.55-5.83 (2H, m), 7.04-8.03 (4H, m), 8.52 (1H, s), 10.14 (1H, s).

EXAMPLE 56

N-[[(2-Oxotetrahydrofuran-3-yl)carbamoyl]amino]-1,2,3,6-tetrahydropyridine mp: 202°-203.5° C.

IR (Nujol): 3350, 1770, 1670, 1530 cm$^{-1}$.

NMR (DMSO-d$_6$, δ): 1.96-2.39 (3H, m), 2.62-2.88 (2H, m), 3.03-3.31 (3H, m), 4.02-4.60 (3H, m), 5.54-5.72 (2H, m), 6.96 (1H, d, J=7 Hz), 7.30 (1H, s).

EXAMPLE 57

N,N'-[Bis-(1,2,3,6-tetrahydropyridin-1-yl)]urea mp: 172°-173.5° C.

IR (Nujol): 3240, 1670 cm$^{-1}$.

NMR (CDCl$_3$, δ): 2.12-2.53 (4H, m), 2.84 (4H, t, J=6 Hz), 3.21-3.50 (2H, m), 5.51-5.70 (2H, m), 6.34 (2H, s).

EXAMPLE 58

N-[(3-Pyrazolylcarbamoyl)amino]-1,2,3,6-tetrahydropyridine mp: 154°-156° C.

IR (Nujol): 3250, 2950, 1660, 1565 cm$^{-1}$.

NMR (DMSO-d$_6$, δ): 2.01-2.40 (2H, m), 2.86 (2H, t, J=6 Hz), 3.12-3.50 (2H, m), 5.53-5.80 (2H, m), 6.28 (1H, d, J=2 Hz), 7.44 (1H, d, J=2 Hz), 7.60 (1H, s), 8.43 (1H, s), 12.11 (1H, s).

EXAMPLE 59

N-[(tert-Butylcarbamoyl)amino]-1,2,3,6-tetrahydropyridine mp: 155.5°-156.5° C.

IR (Nujol): 3350, 3200, 3100, 1675 cm$^{-1}$.

NMR (CDCl$_3$, δ): 1.35 (9H, s), 2.27 (2H, m), 2.85 (2H, t, J=7 Hz), 3.23 (2H, m), 5.27 (1H, s), 5.67 (2H, m), 6.03 (1H, br s).

EXAMPLE 60

N-[(4-Pyridylcarbamoyl)amino]-1,2,3,6-tetrahydropyridine mp: 185°-187° C.

IR (Nujol): 3200, 3100, 1680, 1580 cm$^{-1}$.

NMR (CDCl$_3$, δ): 2.10-2.60 (2H, m), 2.70-3.30 (2H, m), 3.10-3.60 (2H, m), 5.74 (2H, br s), 6.54 (1H, s), 7.30-7.60 (2H, m), 8.30-8.60 (2H, m).

EXAMPLE 61

N-[(3-Pyridylcarbamoyl)amino]-1,2,3,6-tetrahydropyridine mp: 163°-166° C.

IR (Nujol): 3180, 3070, 1667, 1578, 1520-1530 cm$^{-1}$.

NMR (CD₃OD, δ): 2.20–2.60 (2H, m), 2.98 (2H, t, J=6 Hz), 5.72 (2H, s), 7.30–7.50 (1H, m), 7.90–8.30 (2H, m), 8.69 (1H, d, J=2.5 Hz).

EXAMPLE 62

N-[(2-Pyridylcarbamoyl)amino]-1,2,3,6-tetrahydropyridine mp: 163°–164.5° C.

IR (Nujol): 3300, 3200, 3100, 1685, 1650 cm⁻¹.

NMR (CDCl₃, δ): 2.33 (2H, m), 2.97 (2H, m), 3.38 (2H, m), 5.70 (2H, m), 6.35 (1H, s), 6.83–8.28 (4H, m), 8.80 (1H, s).

EXAMPLE 63

N-[[(2-Chloropyridin-5-yl)carbamoyl]amino]-1,2,3,6-tetrahydropyridine mp: 173°–174° C.

IR (Nujol): 3210, 1670, 1460 cm⁻¹.

NMR (CDCl₃, δ): 2.35 (2H, m), 2.98 (2H, m), 3.36 (2H, m), 5.70 (2H, m), 6.45 (1H, s), 7.20 (1H, d, J=8 Hz), 7.97–8.46 (3H, m).

EXAMPLE 64

N-[[(2-Methoxypyridin-5-yl)carbamoyl]amino]-1,2,3,6-tetrahydropyridine mp: 164°–164.5° C.

IR (Nujol): 3350, 1680, 1460 cm⁻¹.

NMR (CDCl₃, δ): 2.33 (2H, m), 2.98 (2H, m), 3.37 (2H, m), 3.90 (3H, s), 5.73 (2H, m), 6.30 (1H, s), 6.73 (1H, d, J=6 Hz), 7.87 (1H, dd, J=6 Hz, 2 Hz), 8.05 (1H, s), 8.18 (1H, d, J=2 Hz).

EXAMPLE 65

N-[(2-Pyrimidinylcarbamoyl)amino]-1,2,3,6-tetrahydropyridine mp: 202°–203° C.

IR (Nujol): 1690 cm⁻¹.

NMR (CDCl₃, δ): 2.37 (2H, m), 3.18 (2H, m), 3.57 (2H, m), 5.77 (2H, m), 6.96 (1H, t, J=5 Hz), 8.65 (2H, d, J=5 Hz), 9.50 (1H, s), 10.16 (1H, s).

EXAMPLE 66

N-[(2-Thiazolylcarbamoyl)amino]-1,2,3,6-tetrahydropyridine mp: 171°–172° C.

IR (Nujol): 3320, 3180, 3100, 1700, 1520 cm⁻¹.

NMR (CDCl₃, δ): 2.42 (2H, m), 3.06 (2H, m), 3.43 (2H, m), 5.78 (2H, m), 6.97 (1H, m), 7.26–7.66 (2H, m), 9.74 (1H, s).

EXAMPLE 67

N-[(1-Pyrrolidinylcarbamoyl)amino]-1,2,3,6-tetrahydropyridine mp: 182.5°–183° C.

IR (Nujol): 1665, 1460 cm⁻¹.

NMR (CDCl₃, δ): 1.81 (4H, m), 2.30 (2H, m), 2.62–3.10 (6H, m), 3.30 (2H, m), 5.67 (2H, m), 6.04–6.56 (2H, m).

EXAMPLE 68

N-[(Morpholinocarbamoyl)amino]-1,2,3,6-tetrahydropyridine mp: 204.5°–205° C.

IR (Nujol): 3230, 1660, 1495, 1460 cm⁻¹.

NMR (CDCl₃, δ): 2.00–2.43 (2H, m), 2.53–3.10 (6H, m), 3.16–3.47 (2H, m), 3.62–3.94 (4H, m), 5.53–5.78 (2H, m), 5.98–6.33 (1H, m), 6.35–6.64 (1H, m).

EXAMPLE 69

N-[(4-Pyridylcarbamoyl)amino]-4-methyl-1,2,3,6-tetrahydropyridine mp: 164.5°–166° C.

IR (Nujol): 3190, 3090, 1685 cm⁻¹.

NMR (CDCl₃, δ): 1.78 (3H, s), 2.01–2.49 (2H, m), 2.67–3.20 (2H, m), 3.20–3.67 (2H, m), 5.23–5.55 (2H, m), 6.54 (1H, s), 7.45 (2H, d, J=5.5 Hz), 8.22–8.68 (3H, m).

EXAMPLE 70

N-[[(6-Methylpyridin-2-yl)carbamoyl]amino]-1,2,3,6-tetrahydropyridine mp: 145.5°–147° C.

IR (Nujol): 3340, 1720 cm⁻¹.

NMR (CDCl₃, δ): 2.03–2.61 (2H, m), 2.41 (3H, s), 2.72–3.12 (2H, m), 3.12–3.68 (2H, m), 5.55–5.81 (2H, m), 6.10–6.60 (1H, m), 8.37–8.88 (1H, s).

EXAMPLE 71

N-[[3-(Dimethylamino)propylcarbamoyl]amino]-1,2,3,6-tetrahydropyridine mp: 86°–88° C.

IR (Nujol): 3400, 1640 cm⁻¹.

EXAMPLE 72

N-[(4-Pyridylcarbamoyl)amino]-5-methyl-1,2,3,6-tetrahydropyridine

IR (Nujol): 3170, 3080, 1675 cm⁻¹.

NMR (CDCl₃, δ): 1.65 (3H, s), 2.10–2.48 (2H, m), 2.51–3.63 (4H, m), 5.38–5.57 (1H, m), 6.44 (1H, s), 7.43 (2H, dd, J=7 Hz, 2 Hz), 8.26–8.55 (3H, m).

EXAMPLE 73

1,1-Diallyl-4-(4-pyridyl)semicarbazide mp: 85.5°–86.5° C.

IR (Nujol): 3240, 1680 cm⁻¹.

NMR (CDCl₃, δ): 3.37 (4H, d, J=5 Hz), 5.11–5.44 (4H, m), 5.63–6.14 (2H, m), 6.43 (1H, s), 7.40 (2H, dd, J=7 Hz, 2 Hz), 8.26 (1H, s), 8.42 (2H, dd, J=7 Hz, 2 Hz).

EXAMPLE 74

N-[[(4-Methylpyridin-2-yl)carbamoyl]amino]-1,2,3,6-tetrahydropyridine mp: 163.5°–165° C.

IR (Nujol): 3320, 3190, 1680 cm⁻¹.

NMR (CDCl₃, δ): 2.14–2.48 (5H, m), 2.70–3.11 (2H, m), 3.16–3.62 (2H, m), 5.56–5.79 (2H, m), 6.30 (1H, s), 6.76 (1H, d, J=6 Hz), 7.93 (1H, s), 8.08 (1H, d, J=6 Hz), 8.75 (1H, s).

EXAMPLE 75

N-[[(3-Methylpyridin-2-yl)carbamoyl]amino]-1,2,3,6-tetrahydropyridine mp: 135.0°–137.0° C.

IR (Nujol) 3220, 1675 cm⁻¹.

NMR (CDCl₃, δ): 2.00–2.54 (5H, m), 2.78–3.66 (4H, m), 5.55–5.86 (2H, m), 6.65–7.08 (2H, m), 7.22–7.61 (2H, m), 7.96–8.30 (1H, m).

What is claimed is:

1. A compound of the formula:

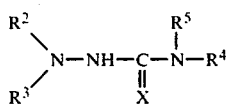

wherein

R² and R³ are taken together with the attached nitrogen atom to form tetrahydropyridyl optionally substituted with lower alkyl, R⁴ is lower alkyl optionally substituted with di(lower-)alkylamino or pyridyl, pyrazolyl, pyridyl optionally substituted with halogen, lower alkyl or lower alkoxy, tetrahydropyridyl, pyrimidinyl, pyrazinyl, pyrrolidinyl, morpholinyl, thiazolyl, thiazolinyl, benzothiazolyl, or tetrahydrofuryl substituted with oxo, R⁵ is hydrogen or lower alkyl, and X is O or S, and a pharmaceutically acceptable salt thereof.

2. A compound of claim 1, wherein

R⁵ is hydrogen, and

X is O.

3. A compound of claim 2, wherein

R⁴ is pyridyl optionally substituted with halogen, lower alkyl or lower alkoxy.

4. A compound of claim 3, which is N-[(4-pyridylcarbamoyl)amino]-1,2,3,6-tetrahydropyridine.

5. A compound of claim 3, which is N-[(3-pyridylcarbamoyl)amino]-1,2,3,6-tetrahydropyridine.

6. A compound of claim 3, which is N-[[(2-chloropyridin-5-yl)carbamoyl]amino]-1,2,3,6-tetrahydropyridine.

7. A compound of claim 2, wherein R⁴ is pyrimidinyl.

8. A compound of claim 6, which is N-[(4-pyrimidinylcarbamoyl)amino]-1,2,3,6-tetrahydropyridine.

9. A process for preparing a compound of the formula:

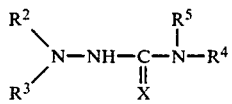

wherein

R² and R³ are taken together with the attached nitrogen atom to form tetrahydropyridyl optionally substituted with lower alkyl, R⁴ is lower alkyl optionally substituted with di(lower-)alkylamino or pyridyl, pyrazolyl, pyridyl optionally substituted with halogen, lower alkyl or lower alkoxy, tetrahydropyridyl, pyrimidinyl, pyrazinyl, pyrrolidinyl, morpholinyl, thiazolyl, thiazolinyl, benzothiazolyl, or tetrahydrofuryl substituted with oxo, R⁵ is hydrogen or lower alkyl, and X is O or S, and a salt thereof which comprises reacting a compound of the formula:

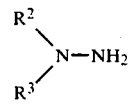

or its salt with a compound of the formula:

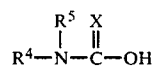

or its reactive derivative or a salt thereof to provide a compound of the formula:

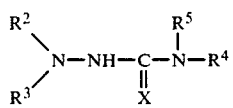

or its salt, in the above formulas R², R³, R⁴, R⁵ and X are each as defined above.

10. An antiinflammatory pharmaceutical composition comprising an anti-inflammatory effective amount of a compound of claim 1, as an active ingredient, in association with a pharmaceutically acceptable, substantially nontoxic carrier or excipient.

11. A method for treatment of inflammation which comprises administering an anti-inflammatory effective amount of a compound of claim 1 to a human being or animal.

12. An analgesic pharmaceutical composition comprising an analgesically effective amount of a compound of claim 1, as an active ingredient, in association with a pharmaceutically acceptable, substantially nontoxic carrier or excipient.

13. A method for treatment of pain which comprises administering an analgesically effective amount of a compound of claim 1 to a human being or animal.

* * * * *